US012797209B2

(12) United States Patent
Beglan

(10) Patent No.: US 12,797,209 B2
(45) Date of Patent: Nov. 17, 2026

(54) RELATING TO A COVERING FOR A PROSTHESIS

(71) Applicant: Philip Beglan, Cotham (GB)

(72) Inventor: Philip Beglan, Cotham (GB)

(*) Notice: Subject to any disclaimer, the term of this patent is extended or adjusted under 35 U.S.C. 154(b) by 521 days.

(21) Appl. No.: 18/480,902

(22) Filed: Oct. 4, 2023

(65) Prior Publication Data

US 2024/0115400 A1 Apr. 11, 2024

(30) Foreign Application Priority Data

Oct. 5, 2022 (GB) ...................................... 2214647
Jun. 14, 2023 (GB) ...................................... 2308872

(51) Int. Cl.
*A61F 2/50* (2006.01)

(52) U.S. Cl.
CPC ........ *A61F 2/50* (2013.01); *A61F 2002/5001* (2013.01)

(58) Field of Classification Search
CPC ...... A61F 2/50; A61F 2002/5001; A61F 2/78; A61F 2/80
See application file for complete search history.

(56) References Cited

U.S. PATENT DOCUMENTS 3,111,683 A * 11/1963 Bach ......................... A61F 2/80 623/38
2007/0150069 A1* 6/2007 Takami ..................... A61F 2/60 623/27
2022/0039975 A1* 2/2022 Hillmann .............. A61F 2/7812

* cited by examiner

*Primary Examiner* — Yashita Sharma
(74) *Attorney, Agent, or Firm* — Maine Cernota & Curran

(57) ABSTRACT

A structure for covering a prosthetic limb, the structure comprising: a fabric comprising a plurality of weft strands and at least one warp element; a substantially rigid support configured to run along the part of the structure which deforms least with movement of the structure; and wherein the plurality of weft strands of the fabric are attached to the substantially rigid support at a plurality of points such that the weft strands pivots independently of the substantially rigid support with movement of the structure.

20 Claims, 9 Drawing Sheets

30
26
16
14
10
28a
28b
14
30
28d
28c
38
40
34
36
32
42
22

RELATING TO A COVERING FOR A PROSTHESIS

RELATED APPLICATIONS

This application claims priority to UK Application No. 2308872.7, filed Jun. 14, 2023, and to UK Application No. 2214647.6, filed Oct. 5, 2022. These applications are herein incorporated by reference, in their entirety, for all purposes.

FIELD OF THE INVENTION

The present invention relates to the field of prosthesis coverings, and in particular, to a structure for covering a prosthetic limb comprising a fabric and a substantially rigid support.

BACKGROUND OF THE INVENTION

Prosthesis coverings have the ability to change the aesthetics of a prosthetic. The appearance of a prosthetic limb can be important to the individual wearing the prosthesis, and therefore prosthesis coverings can positively impact the wearer's psychological wellbeing and body image.

Despite the importance of prosthesis coverings, the satisfaction levels of amputees regarding prosthesis coverings have been reported to be low, and areas where design improvements and further research are required have been identified.

Prioritized areas for improvement include: increasing the life of the prosthesis covering, increasing the life-likeness of the shape of the covering, and improving the ease of removal of the covering from the prosthetic limb such that the prosthetic limb can be more easily accessed for maintenance for example.

Increasing the life-like shape and natural movement of a prosthetic covering is particularly challenging for joints such as the knee which do not pivot around one axis. Instead, the knee travels back and down when moved, which is a challenge to replicate in traditional prosthesis coverings.

Conventional prosthesis coverings are a combination of a silicone outer casing filled with foam which contacts the prosthetic limb. In addition, to an unnatural motion, a silicone/foam prosthesis covering has a poor durability, as the foam is worn away rapidly against the metal workings of the prosthetic limb.

Silicone/foam prosthesis coverings are typically glued to the prosthetic limb, therefore making removal of the covering for prosthetic limb maintenance difficult. Additionally, the permanence of gluing the covering to the prosthetic limb means the wearer is unable to make spontaneous decisions as to whether, or how, they would like to cover their prosthesis. With a more easily removable covering, it can be envisioned that the wearer may decide whether to cover their prosthetic limb depending on the given day or situation.

Furthermore, conventional prosthesis coverings are expensive which increases the importance of improving the life time of the coverings. A cost-effective prosthesis covering would also increase the accessibility of coverings to a wider range of prosthesis wearers.

Therefore, there is a requirement for a prosthesis covering with an improved life-like shape and movement. The solution is required to be inexpensive such that it can be made widely available to prosthesis wearers, and should also have an improved means of attaching and detaching the covering to the prosthetic limb such that the wearer can experience an increased ease of use.

It is against this background that the present invention has arisen.

SUMMARY OF THE INVENTION

According to the present invention, there is provided a structure for covering a prosthetic limb, the structure comprising: a fabric comprising a plurality of weft strands and at least one warp element; a substantially rigid support configured to run along the part of the structure which deforms least with movement of the structure; and wherein the plurality of weft strands of the fabric are attached to the substantially rigid support at a plurality of points such that the weft strands pivot independently of the substantially rigid support with movement of the structure.

In some embodiments, a structure may be provided for covering a prosthetic limb, the structure comprising: a fabric comprising a plurality of weft strands; one or more cables attached to the plurality of weft strands of the fabric; a substantially rigid support configured to run along the part of the structure which deforms least with movement of the structure; and wherein the plurality of weft strands of the fabric are attached to the substantially rigid support at a plurality of points such that the weft strands pivot independently of the substantially rigid support with movement of the structure.

The present invention relates to a structure for covering a prosthetic limb comprising a plurality of weft strands attached to a substantially rigid support such that the weft strands pivot independently of the substantially rigid support. This is in contrast to other prosthesis coverings in which pressure must be applied to compress a volume of foam when the covering moves. Therefore, the present invention is a covering for a prosthetic limb with an improved ability to follow the movement of the prosthetic limb. The present invention is thus a prosthesis covering with an improved life-like movement.

Within the context of the present invention, the term 'prosthetic limb' should be understood to refer to any form of prosthetic limb, and is not limited to a particular body part, for example. In some embodiments, the prosthetic limb may be a prosthetic leg, or may be a prosthetic arm or may be any other body part. It may be sized for an adult or a child. Furthermore, the term 'prosthetic limb' should be understood to not be limited to the field of human prosthetics. The present invention is equally applicable to the fields of puppetry and/or robotics, for example.

In some embodiments, the substantially rigid support runs along the neutral zone where the surface of the structure largely does not stretch or compress when the prosthetic limb bends. Within the context of the present invention, the term 'substantially rigid' should be understood to refer to a support which is rigid along the majority of its length. In some embodiments, the rigid support may comprise one or more sections which have a degree of flexibility. For example, the rigid support may have a degree of flexibility as it runs along a joint, to enable the support to bend as the joint moves. In some embodiments, the substantially rigid support acts as a frame for the fabric to be attached to via the plurality of weft strands. In some embodiments, the substantially rigid support has a degree of flexibility. In some embodiments, the substantially rigid support may have sufficient flexibility to enable the structure to follow a twisting movement of the prosthetic limb.

The term "fabric" as used herein should be understood to refer to any material comprising at least a plurality of weft strands, at least one warp element, and may include a woven, knitted or 3D printed material. However, other materials, formed by other processes may also be included within the meaning of the term. In some embodiments, the structure of the present invention comprises a fabric which facilitates a compliant structure, that more accurately replicates the movement of a joint, compared to known prosthesis coverings. In some embodiments, the structure of the present invention may have an increased durability compared to known prosthesis coverings, because the fabric may reduce the number of mechanical parts required.

In some embodiments, the fabric comprising a plurality of weft strands attached to the substantially rigid support at a plurality of points is important to ensure the volume changes within the structure are organized as the prosthetic limb and covering bend.

Such embodiments contrast with known prosthesis coverings, which may comprise a number of discrete, spaced sections in the area of a joint. The sections are typically at right angles to the curve of the prosthetic and are separated by gaps between each section. As the prosthetic moves, the sections fan out from one another in order to accommodate the movement. The range of motion of this type of prosthetic covering is limited, and this type of structure cannot emulate the full range of motion of a joint such as a knee or an elbow. In contrast with known prosthesis coverings, by attaching a plurality of weft strands to the substantially rigid support such that they can pivot independently, the structure of the present invention can move with an increased smoothness and with a constant curvature that better emulates the movement of a limb.

In some embodiments, the ability of the plurality of weft strands to pivot independently of the substantially rigid support creates a more even deformation of the covering with movement by enabling the surface of the fabric to stretch and compress along its entire length. In some embodiments, the substantially rigid support comprises a degree of flexibility as it runs along a joint, enabling the support to adapt to the movement of the prosthesis, and the independent pivoting of the weft is able to comply with that curve. This is in contrast to known coverings, as mentioned above, where the weft strands are constrained at a right angle to the curve. In some embodiments, this eases the amount of stretch required at the maximum stretch area. For example, in the embodiment in which the prosthetic limb is a prosthetic leg, when the knee bends, the fabric may stretch all the way along the thigh which eases the amount of stretch required at the maximum stretch area at the front of the knee. This even deformation can reduce local stress on the structure, reducing wear and tear and prolonging the lifetime of the covering.

In some embodiments, the fabric may be just a few mm thick. In some embodiments, in which the structure covers a prosthetic leg for example, it may be advantageous for the structure to be just a few mm thick at the inner thigh in order to improve the comfort for the wearer. The provision of a thin structure, of just a few mm at the inner thigh, ensures that the prosthesis does not rub against the user's other inner thigh. This may also prevent wear of the structure in areas where friction is likely and therefore improves the durability of the structure.

In some embodiments, the fabric may be manufactured and attached to the substantially rigid support as discrete patches via the plurality of weft strands.

In some embodiments, a structure for covering a prosthetic limb comprising a fabric may be a cost-effective alternative to conventional prosthetic limb coverings which facilitates the covering being accessible to a wide range of prosthetic limb wearers.

In some embodiments, the structure may comprise one or more cables attached to the plurality of weft strands of the fabric. In some embodiments, the structure may not comprise cables, and the shape and/or movement of the fabric may be controlled by the plurality of weft strands and the warp element or elements. In some embodiments, the structure may comprise one or more removable cables, such that the structure is adaptable to different situations and preferences of the user. In some embodiments, the cables may be removed from the structure when the wearer prefers a more compliant structure.

In some embodiments, it may be preferable for the structure to comprise one or more cables, in order to enable a more controlled and organized deforming of the structure. In some embodiments, the shape of the structure may be provided by one or more cables attached to the plurality of weft strands. In some embodiments, the one or more cables help to guide the bending of the structure when the prosthetic limb moves. In some embodiments, the one or more cables prevent the covering from bending at the weakest point and instead facilitate the structure following the movement of the prosthetic limb. In some embodiments, the combination of the fabric and the one or more cables facilitates the restoration of the volume of the missing limb, which can improve the overall aesthetic of the prosthetic limb and covering. The covering of the present invention can therefore help to improve the body image of the wearer.

In some embodiments, the one or more cables may be attached to the weft strands such that they are "free-riding" and can slide through the fabric to guide the bending of the structure. In some embodiments, the cables may be attached to the weft strands of the fabric by spring sheaths. In some embodiments, the spring sheath may have sufficient spring to organize the weft strands with movement of the structure. In some embodiments, the cables may be attached to the weft strands of the fabric using tube sheaths. In some embodiments, the sheaths may be sprung or may be passive. In some embodiments, the cables may be attached to the weft strands with eyelets. In some embodiments, the cables may be stitched onto the weft strands. In some embodiments, in which the fabric is knitted or woven, the cables may run through channels in the fabric. In some embodiments, the cables may run through channels in the substantially rigid support. In some embodiments, in which the fabric is a 3D lattice, the cables may run through the lattice. In some embodiments, the cables may run through loops created by the warp strands of the fabric. In some embodiments, the cables may run in between two weft strands. In some embodiments, in which the structure is a covering for a prosthetic leg, at least one cable may run down the back of the calf area of the structure. In some embodiments, at least one cable may run down the side of the knee area of the structure. In some embodiments, two cables may run down the back of the calf which can increase the stability of the structure at the knee. In some embodiments, there may be two cables running down the front of the knee.

In some embodiments, the fabric may further comprise one or more warp strands. In some embodiments, the fabric may comprise a plurality of weft and warp strands. In some embodiments, the fabric may comprise a plurality of weft and warp strands arranged in a variety of configurations depending on the desired characteristics of the covering.

In some embodiments, the fabric may be woven. In some embodiments, the plurality of weft and warp strands may be woven together to form a fabric. In some embodiments, the fabric may be knitted. In some embodiments the fabric may comprise a plurality of weft and warp strands which are configured to form a knitted fabric.

In some embodiments, the fabric may be 3D printed. In some embodiments, the fabric may be a 3D printed lattice which combines weft and warp strands. For example, the 3D printed fabric may have a waffle-like structure. In some embodiments, the plurality of weft strands may be 3D printed to form a spring which also acts as a contactable/expandable coil in the warp direction. In some embodiments, the 3D printed lattice may be silicone. In some embodiments, a 3D printed fabric may be advantageous in creating a covering which is easy to clean.

In some embodiments, the structure may further comprise a second plurality of weft strands. In some embodiments, the structure may comprise more than two pluralities of weft strands. In some embodiments, the structure may comprise a second plurality of weft strands provided on the inside of the structure. In some embodiments, the second plurality of weft strands may be elastic. In some embodiments, the additional plurality of weft strands may provide the fabric with a bias to form a curve. In some embodiments, the second plurality of weft strands may enable the fabric to have ‘memory’.

The term “memory” as used herein should be understood to refer to any fabric configuration in which the fabric regains its equilibrium, its curve, and its place after application of pressure. The fabric may regain its equilibrium, its curve, and its place in relation to the sliding cable after application of pressure. In some embodiments, the fabric may contract easily lengthwise and have sufficient elasticity to guide the plurality of weft strands to spread easily.

In some embodiments, the second plurality of weft strands may enable the fabric to have a flesh like local deformation when for instance a finger pushes on the fabric. In some embodiments, the second plurality of weft strands may enable the fabric to have a more general deformation such as the thigh cushioning when sitting on a chair.

In some embodiments, the first plurality of weft strands may comprise eyelets and the eyelets may guide the second plurality of weft strands on the inside of the structure, such that the second plurality of weft strands are substantially in line with the first plurality of weft strands. In some embodiments, the second plurality of weft strands may be stitched to the first plurality of weft and/or first plurality of warp strands.

In some embodiments, the first plurality of weft strands may comprise spacers on the inside of the structure, and the spacers may guide the second plurality of weft strands on the inside of the structure, such that the second plurality of weft strands are substantially in line with the first plurality of weft strands. In some embodiments, the spacers make it possible to create an exact contour.

In some embodiments, the second plurality of weft strands may be springs. In some embodiments, the springs may be provided on the inside of the structure or the outside of the structure such that they are pushing inwards or outwards. In some embodiments, the second plurality of weft strands may comprise springs with a cord through the spring which can prevent the weft from flattening out.

In some embodiments, each of the first plurality of weft strands may be housed in a tube. In some embodiments, the tube housing each weft strand may have slits on the inner side of the structure. In some embodiments, the elasticity of the first plurality of weft strands provides them with a bias to form a curve which closes the slits in the tube housing. The tube housing is therefore able to adapt to the movement and curvature of the fabric.

In some embodiments, the structure may comprise a second plurality of warp strands. In some embodiments, the second plurality of warp strands may form a woven fabric with the second plurality of weft strands. In some embodiments, a first and second woven fabric may be joined such that the structure has an inner and an outer woven fabric. In some embodiments, the inner woven fabric may pull inwards whilst the outer woven fabric may push outwards, therefore providing the structure with compression and/or tension and ‘memory’.

In some embodiments, in which the fabric is 3D printed, the fabric may be printed as substantially one piece. In some embodiments, the 3D printed fabric may be substantially made of one material. In the embodiment that the 3D printed fabric comprises a plurality of first and second weft strands and/or first and second warp strands, all of the weft and warp strands may be substantially the same material. Such embodiments may realize an increased ease and cost effectiveness of manufacturing.

In some embodiments, the 3D printed fabric may be printed substantially flat and the curvature of the fabric may be subsequently activated. In some embodiments, the 3D printed fabric may be assembled by pulling one or more weft strands. In some embodiments, by pulling one or more of the weft strands, the inner weft may shorten. In some embodiments, as the inner weft shortens, it may snap into place, forming a curved surface. In some embodiments, the inner weft may comprise an arrow shaped formation along the weft which passes through a hole, enabling the inner weft to snap into place, and retain a curved structure. In some embodiments, the hole may be an eyelet. In some embodiments, the 3D printed fabric may comprise rows of eyelets, and the hole through which the arrow formation snaps, may be the last eyelet in the row.

In some embodiments, printing the 3D printed fabric substantially flat, and subsequently curving the fabric, can be quicker and more cost effective than printing a curved structure.

In some embodiments, in which the 3D printed fabric is printed substantially flat, the 3D printed fabric may be subsequently attached to an outer layer. In some embodiments, the 3D printed fabric may be glued to an outer layer. In some embodiments, the outer layer may be a fine mesh covering. In some embodiments, the 3D printed fabric can be used to form a composite structure. In some embodiments, printing the 3D printed fabric as a flat structure enables easy assembly of a composite structure.

Alternatively, the 3D printed fabric may be printed as a curved structure. In some embodiments, the 3D printed fabric may be printed in its final shape. In such embodiments, it is possible to print the inner and outer weft as a single unit. In this embodiment, the fabric may be a flexible material such as, but not limited to, thermoplastic polyurethane (TPU). In this embodiment, the curvature of the fabric is provided without the requirement to pull the inner weft. In this embodiment, the inner weft does not ride through eyelets, and is instead a single piece without eyelets.

In some embodiments, the fabric may be printed in its final curved state as a single weft fabric. Such embodiments may be useful for covering narrower portions of a prosthetic limb, where a thinner covering may be preferred as there is less room for a double weft and less need for a cushioning effect. Such embodiments may be suited to covering a prosthetic arm or an ankle, for example. In such embodiments, the printed material of the single weft and its thickness may determine the rigidity of the weft.

In some embodiments, the size of the 3D printed fabric may be fully customizable and may be printed according to the dimensions of the wearer. In some embodiments, by printing the 3D printed fabric substantially flat and subsequently activating the curvature of the fabric, the size and curvature of the fabric can be adjusted and optimised to match the curvature of the prosthesis and/or the limb being replicated.

In some embodiments, the structure may be substantially hollow. In some embodiments, different brands of prosthetic limbs may use a different pivoting mechanism at the joints. The structure being substantially hollow facilitates compatibility with a wide range of prosthetics. In some embodiments, the hollow nature of the structure enables the structure to adapt to the shape and follow the movement of a wide range of prosthetic limbs without being limited to a certain brand. Therefore the hollow nature of the structure facilitates it being suitable for a wide range of prosthetic limb users.

In some embodiments, a substantially hollow covering can also increase the durability of the covering compared to conventional silicone/foam coverings in which the silicone covering is typically filled with foam. Any foam in contact with the metal socket of the prosthetic inside the covering is prone to being sliced and worn by the inner workings of the prosthetic. Therefore a substantially hollow covering eliminates this problem and can prolong the life of the covering.

In some embodiments, an assembly comprising a prosthetic limb and a structure as described herein may be provided. In some embodiments, the assembly may comprise a prosthetic limb which may be a prosthetic arm. In some embodiments, the structure may be a covering for a prosthetic limb which may be a prosthetic arm. In some embodiments, the assembly may comprise a prosthetic limb which may be a prosthetic leg comprising one or more of: an ankle joint; a knee joint; a pylon connecting the ankle joint and the knee joint and configured to form a prosthetic shin; a means for attaching the prosthetic leg to a residual leg; and a length connecting the knee joint to the means for attaching the prosthetic leg to the residual leg, and wherein the length is configured to form a prosthetic thigh. In some embodiments, the structure may be a covering for a prosthetic limb which may be a prosthetic leg comprising one or more of: an ankle joint; a knee joint; a pylon connecting the ankle joint and the knee joint and configured to form a prosthetic shin; a means for attaching the prosthetic leg to a residual leg; and a length connecting the knee joint to the means for attaching the prosthetic leg to the residual leg, and wherein the length is configured to form a prosthetic thigh. In some embodiments, the structure may be integrated with the prosthesis.

In some embodiments, the structure may further comprise a means for attaching the structure to the prosthetic limb. The structure may be attached to the prosthetic limb in various ways.

In some embodiments, the means for attaching the structure to the prosthetic limb may comprise an upper band attached to the fabric or to the substantially rigid support of the structure. In some embodiments, the substantially rigid body may splay at the top of the structure to provide a greater area for attachment of the upper band to the structure. The upper band itself may be a mesh such that it compresses. The upper band may have tension lengthwise and have a stretch which can be used to attach to the prosthetic and withstand push and pull of the fabric when in use. In some embodiments, the cables may attach to the upper band of the structure.

In some embodiments, the means for attaching the structure to the prosthetic limb enables easy attachment and/or detachment of the covering from the prosthetic by the wearer. In some embodiments, this enables the user to easily fit and/or remove the covering themselves. In some embodiments, this enables the user to clean the covering and to easily access the prosthetic limb for maintenance which is in contrast to coverings which are glued to the prosthetic.

In some embodiments, the substantially rigid support may comprise a means for attaching the structure to the prosthetic limb. In some embodiments, the substantially rigid support may comprise a means of attaching onto or around the pylon between the knee and the foot. In some embodiments, the means for attaching the structure to the prosthetic limb may comprise a means which corresponds to and interacts with or "clicks-on" to a means provided on the pylon of the prosthetic limb such that the structure is attached to the prosthetic limb.

In some embodiments, the means for attaching the structure to the prosthetic limb may comprise a strap provided to the bottom of the structure and which may sit under a prosthetic foot when the covering is in use.

In some embodiments, the structure may be fitted onto a prosthetic limb by sliding the structure onto the bottom of the prosthetic limb and pulling the structure into place. In some embodiments, in which the prosthetic limb is a prosthetic leg, the foot at the end of the prosthesis may be removed from the prosthetic limb to facilitate the fitting of the structure. In some embodiments, the structure may further comprise a zip. In some embodiments, the zip may be provided alongside the substantially rigid support. In some embodiments, a zip may facilitate the attachment and/or detachment of the covering to the prosthetic limb. In some embodiments, the zip can facilitate the wearer in putting on and taking off the structure by themselves. In some embodiments, the structure may alternatively or additionally comprise a hook and loop fastener such as Velcro®. Alternatively or additionally, the structure may comprise any other standard means of clothing fastening.

In some embodiments, in which the prosthetic limb is a prosthetic leg, the substantially rigid support of the structure may run between the ankle of the prosthetic leg and the means for attaching the prosthetic leg to a residual leg.

In some embodiments, in which the prosthetic limb is a prosthetic leg, the substantially rigid support of the structure may run along the middle of both the inside and outside of the prosthetic thigh, when the prosthetic thigh is viewed from the side.

In some embodiments, the substantially rigid support of the structure may comprise one or more flexible portions. In some embodiments, the support may be rigid along the majority of its length, and may comprise one or more sections having a degree of flexibility. In some embodiments, the substantially rigid support may comprise a flexible spine at one or more joints of the prosthetic limb. For example, in the embodiment in which the prosthetic limb is a prosthetic leg, the substantially rigid support may comprise a flexible spine at the knee and/or ankle. In some embodiments, the substantially rigid support may comprise a flexible portion at the knee joint which curves from the prosthetic thigh to the top of the prosthetic shin.

In some embodiments, by comprising one or more flexible portions at one or more joints, the structure may have an improved ability to follow the movement of the prosthetic limb. In some embodiments, the one or more flexible portions may enable the structure to adapt to the variety of pivot movements of the prosthetic joints. In some embodiments, this may facilitate the cover being suitable for covering different types of prosthetic limb which may comprise different movement mechanisms.

In some embodiments, the substantially rigid support of the structure may run along the prosthetic shin. In some embodiments, at the knee the substantially rigid support may curve forward to the top/front of the shin and then gently out as it goes down the shin. In some embodiments, the substantially rigid support of the structure may run along the inside and the outside of the prosthetic ankle joint.

In some embodiments, the structure may further comprise an outer layer. In some embodiments, the outer layer may be a silicone top layer. In some embodiments, the outer layer may be a stocking, a sock, a pair of trousers or a skirt. In some embodiments, the structure of the present invention is suitable for use with a stocking outer layer because of the even deformation of the structure created by the arrangement of the fabric and the plurality of weft strands. In some embodiments, the even deformation reduces the amount of stretch required at the maximum stretch areas such as the front of the knee, which enables stockings to be worn over the top of the structure.

In some embodiments, the structure of the present invention is suitable for use with an outer layer because it provides a continuous surface onto which an outer layer can be placed. This contrasts with known prosthesis coverings, which can comprise a number of discrete, spaced sections, separated by gaps. When used with an outer covering, the outer covering may sink into the gap created between the sections. Therefore, the continuous surface of the present invention enables a more aesthetically pleasing outer layer, which better emulates the volume of a limb compared to typical prosthesis coverings.

BRIEF DESCRIPTION OF THE DRAWINGS

The present invention will now be described, by way of example only, with reference to the accompanying figures in which.

DETAILED DESCRIPTION

Figure 1A:
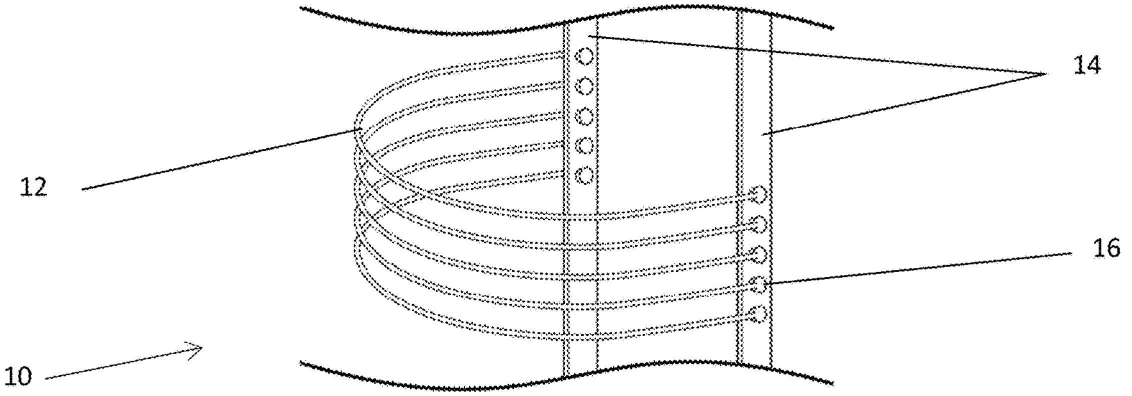
FIG. 1A shows a plurality of weft strands attached to a substantially rigid support.

The present invention relates to a structure 10 for covering a prosthetic limb. As shown in FIG. 1A, the structure comprises a fabric comprising a first plurality of weft strands 12 and at least one warp element (not shown). The first plurality of weft strands 12 are attached to a substantially rigid support 14 at a plurality of points 16 such that the first plurality of weft strands 12 can pivot independently of the substantially rigid support 14 with movement of the structure 10.

Figure 1B:
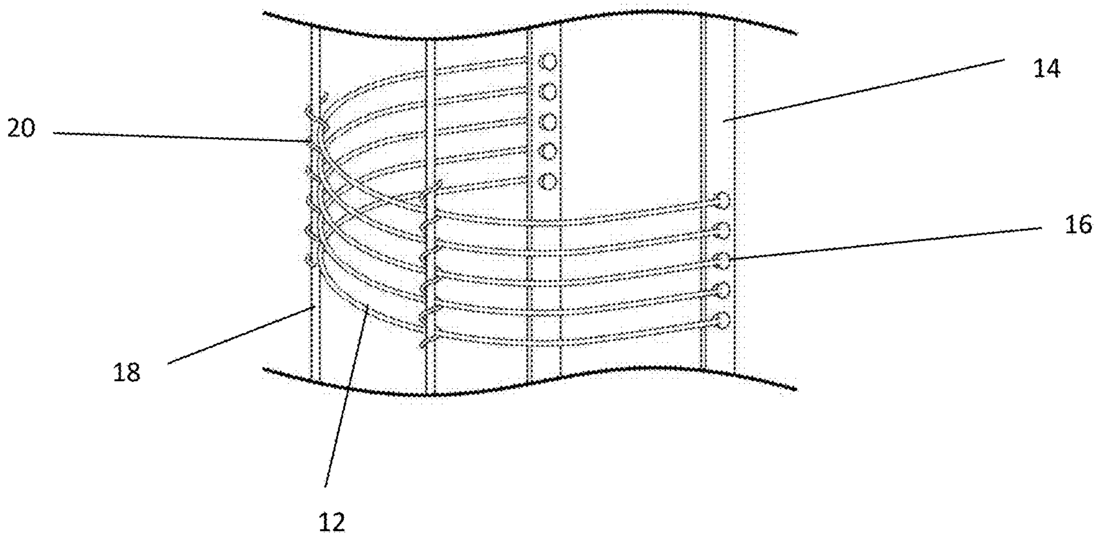
FIG. 1B shows cables attached to the plurality of weft strands of FIG. 1A.

The structure 10 may additionally comprise one or more cables 18 as shown in FIG. 1B. The cables 18 are attached to the first plurality of weft strands 12 for example via a spring sheath 20. Alternatively or additionally, the cables 18 may be attached to the first plurality of weft strands 12 via tube sheaths, eyelets or may be stitched onto the fabric. Alternatively or additionally, the cables 18 may run through channels 43 (see FIG. 4B) in the fabric and/or substantially rigid support 14. The structure 10 may be substantially hollow.

Figure 2A:
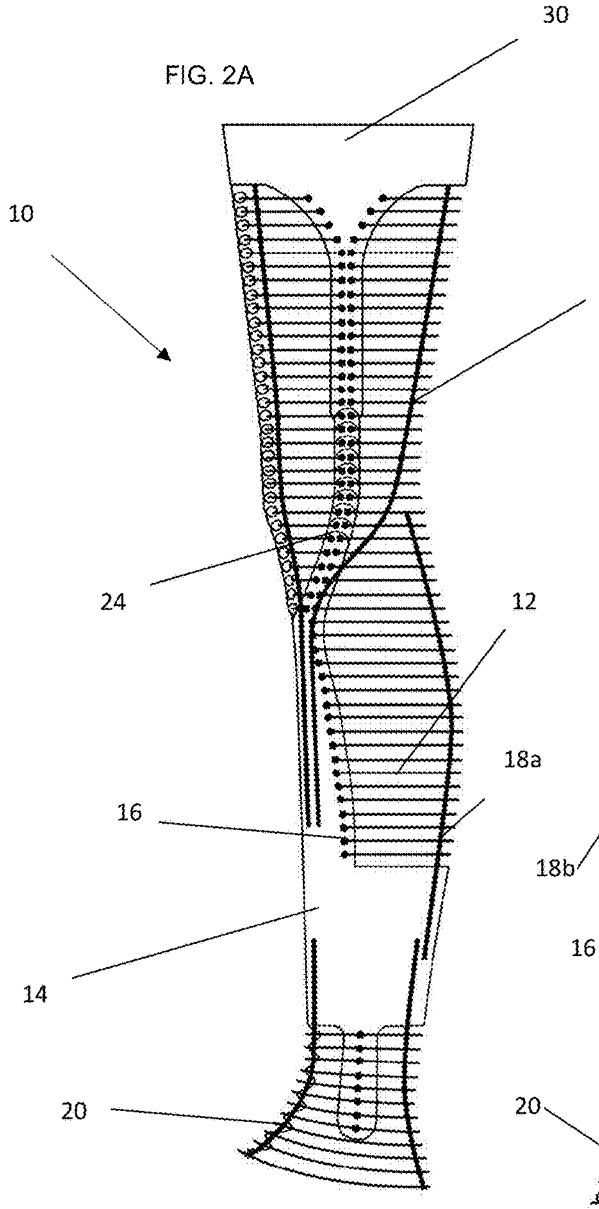
FIG. 2A shows a prosthetic leg covering, viewed from the side.
Figure 2B:
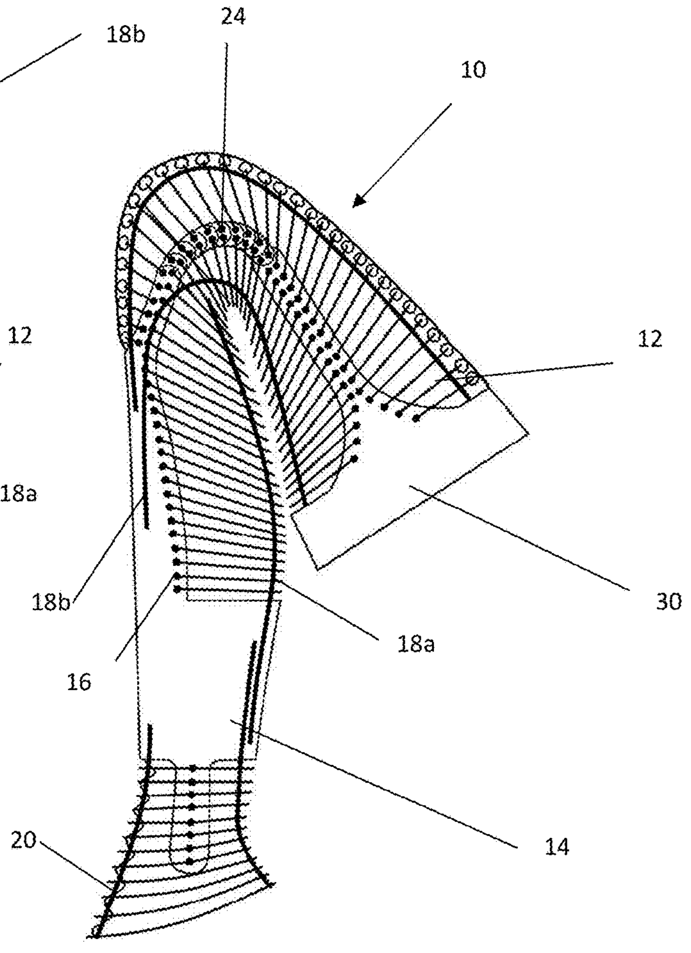
FIG. 2B shows the prosthetic leg covering of FIG. 2A as the prosthetic leg covering bends.

As shown in FIG. 2A, the structure 10 may be a covering for a prosthetic leg 22 (see FIG. 3). The substantially rigid support 14 is configured to run along the part of the structure 10 which deforms least with movement of the structure 10. The substantially rigid support structure 14 comprises a flexible portion 24 at the knee of the prosthetic leg 22 to facilitate the structure 10 following the movement of the prosthetic leg 22. As illustrated by FIG. 2B, as the prosthetic leg 22 bends, the substantially rigid support 14 runs along the neutral zone and largely does not stretch or compress. The first plurality of weft strands 12 pivot independently of the substantially rigid support 14, ensuring the volume changes within the structure are organised as the structure 10 bends. The pivoting of the first plurality of weft strands 12 enables the fabric to stretch and compress along its entire length which eases the amount of stretch required at the maximum stretch area at the front of the knee.

As illustrated by FIG. 2, the structure 10 may have at least one cable 18*a* running down the back of the calf area of the structure 10. Alternatively or additionally, at least one cable 18*b* may run down the side of the knee area of the structure. The structure 10 may further comprise an upper band 30 attached to the fabric and/or to the substantially rigid support 14 to attach the structure 10 to the prosthetic leg 22. The upper band 30 and/or substantially rigid support 14 may be provided with channels to receive the loose end of the cables 18.

Figures 3A, 3B, 3C:
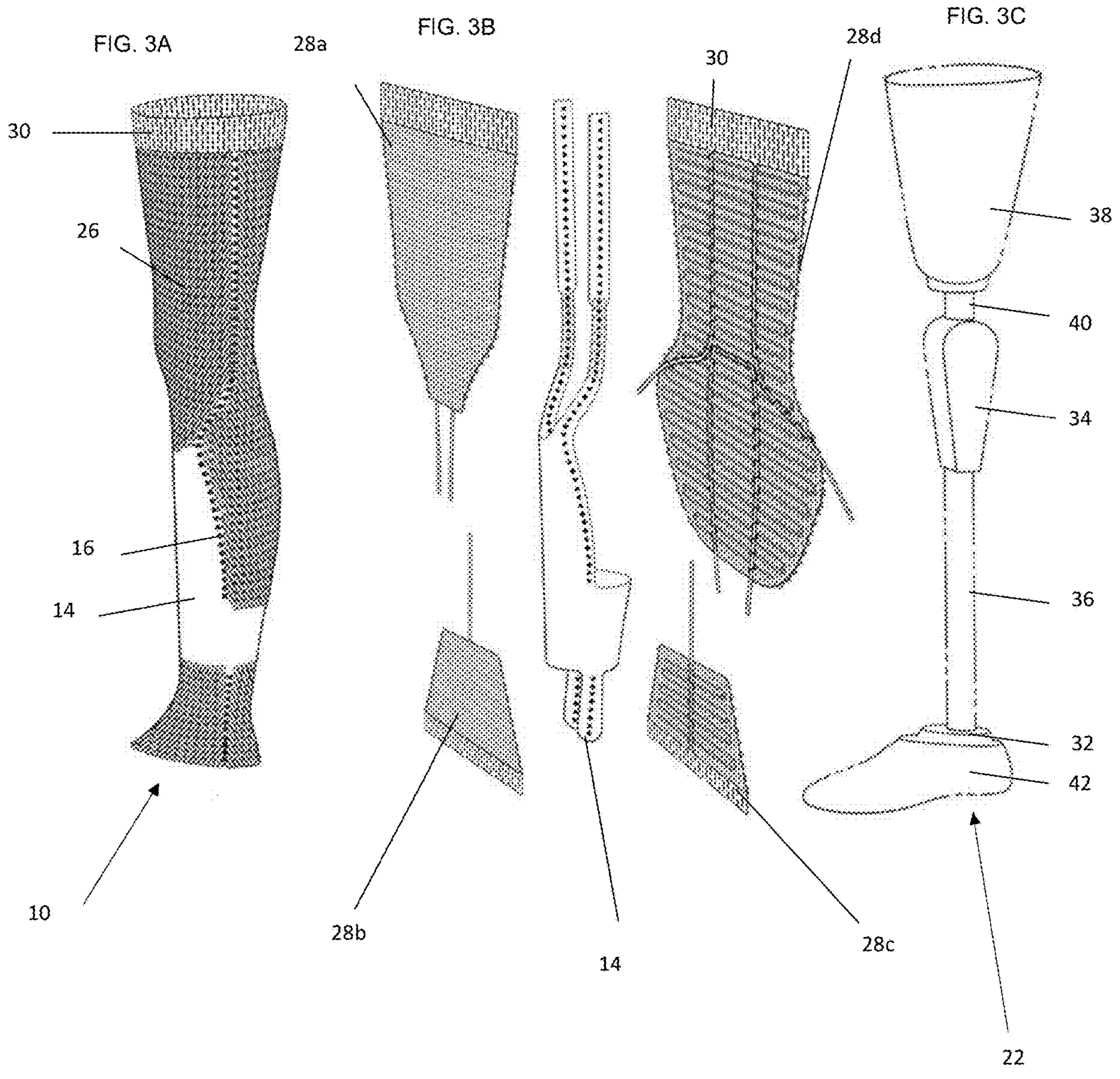
FIG. 3A shows a prosthetic leg covering comprising a woven fabric, viewed from the side.
FIG. 3B shows the prosthetic leg covering of FIG. 3A with woven fabric panels.
FIG. 3C shows a prosthetic leg to which the covering of FIGS. 3A and 3B may be fit.

As shown in FIG. 3A, the fabric may additionally comprise a plurality of warp strands 68 (see FIG. 6B) which may be configured to form a woven fabric 26 with the first plurality of weft strands 12. Alternatively, the plurality of warp strands 68 may form a knitted fabric with the first plurality of weft strands 12. As shown in FIG. 3B, the woven fabric may be created as a number of woven panels 28*a*, 28*b*, 28*c* and 28*d* which are subsequently attached to the substantially rigid support 14 via attachment of the first plurality of weft strands 12 at a plurality of points 16.

The structure 10 may comprise a means of attaching the structure to a prosthetic limb such as a prosthetic leg 22, as shown in FIG. 3C. The prosthetic leg may comprise an ankle joint 32, a knee joint 34, a pylon 36 connecting the ankle joint 32 and the knee joint 34 and configured to form a prosthetic shin, a means for attaching the prosthetic leg to a residual leg 38, and a length 40 connecting the knee joint 34 to the means for attaching the prosthetic leg to the residual leg 38, and wherein the length 40 is configured to form a prosthetic thigh. The ankle joint 32 may be attached to a prosthetic foot 42. The means of attaching the structure 10 to the prosthetic leg 22 may be an upper band 30 attached to the fabric and/or to the substantially rigid support 14 of the structure 10. The substantially rigid support 14 of the structure 10 may run between the ankle joint 32 of the prosthetic leg 22 and the means for attaching the prosthetic leg to a residual leg 38. The substantially rigid support 14 of the structure 10 may run along the middle of both the inside and outside of the prosthetic thigh, when the prosthetic thigh is viewed from the side. The substantially rigid support 14 of the structure 10 may run along the prosthetic shin. At the knee joint 34 the substantially rigid support 14 may curve forward to the top/front of the shin and then gently out as it goes down the shin. The substantially rigid support 14 of the structure 10 may run along the inside and the outside of the prosthetic ankle joint 32.

Figure 4:
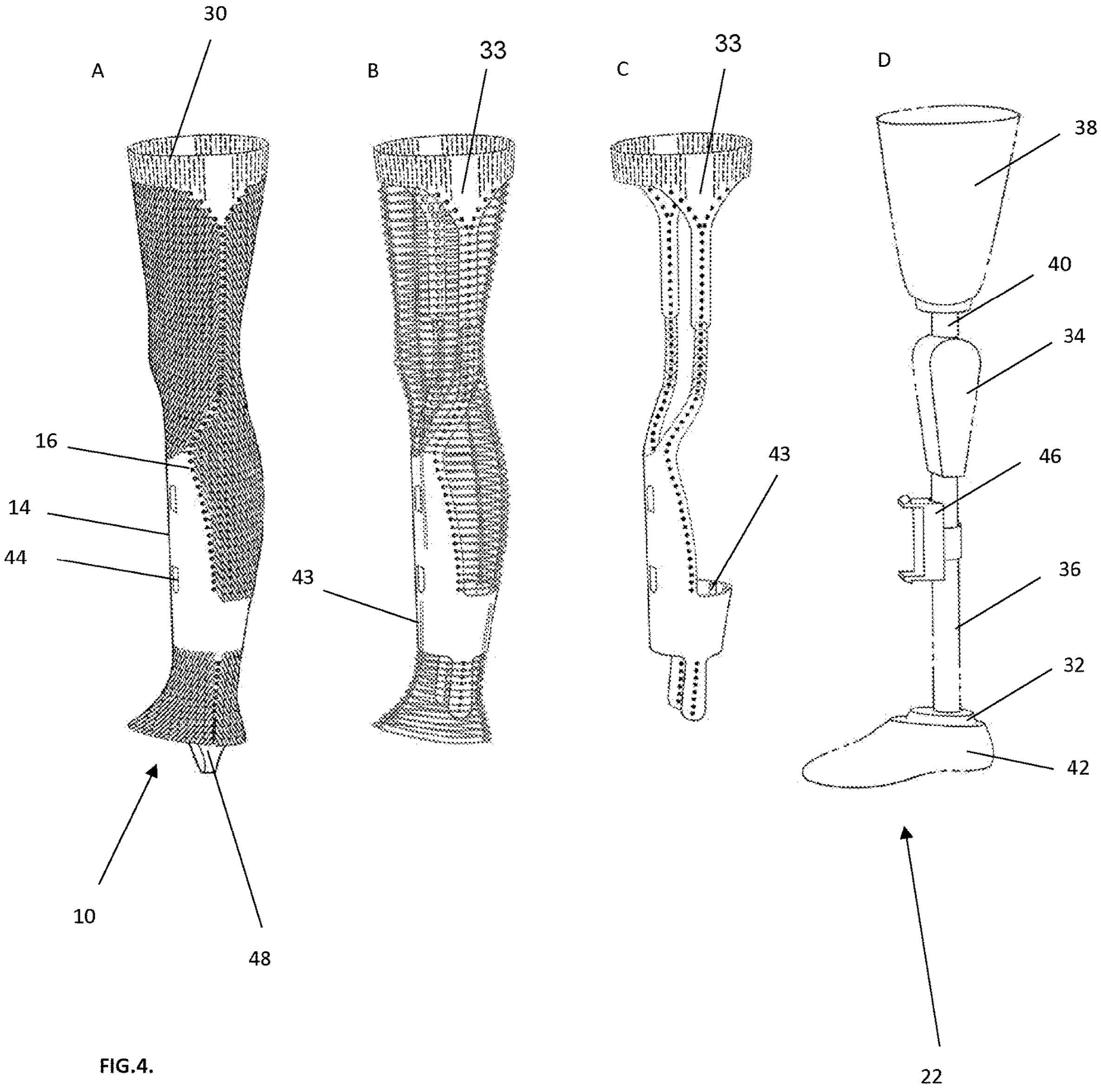
FIG. 4A shows a prosthetic leg covering with means for attaching to a prosthetic leg, viewed from the side.
FIG. 4B illustrates the arrangement of the plurality of weft strands within the prosthetic leg covering of FIG. 4A.
FIG. 4C illustrates the substantially rigid support within the prosthetic leg covering of FIG. 4A.
FIG. 4D shows a prosthetic leg with attachment means.

As shown in FIGS. 4B and 4C, the substantially rigid support 14 may splay at the top of the structure 10 as indicated by reference marker 33 to provide a greater area for attachment of the upper band 30 to the structure 10. The upper band 30 itself may be a mesh such that it compresses. The upper band may have a tension lengthwise and a stretch which can be used to attach to the prosthetic leg 22 and withstand push and pull of the fabric when in use. The cables 18 may also attach to the upper band 30.

Referring to FIGS. 4A to 4C, the substantially rigid support 14 may comprise a means of attaching onto or around the pylon 36 between the knee 34 and the ankle joint 32. The substantially rigid support 14 may comprise a means which interacts with a corresponding piece 46 provided to the prosthetic leg 22, as shown in FIG. 4D. The substantially rigid support 14 may be provided with holes 44 which interact with a protruding portion of the piece 46 on the prosthetic leg 22 such that the support 'clicks-on' to the prosthetic leg 22. The structure 10 may alternatively or additionally comprise a strap 48 provided to the bottom of the structure 10 and which may sit under the prosthetic foot 42 when the structure 10 covers the prosthetic leg 22. The structure 10 may further comprise a zip, a hook and loop fastener such as Velcro®, or any other means of attachment (not shown). As shown in FIG. 4B, the substantially rigid support 14 may be provided with channels 43 on the inside of the structure 10 through which the cables 18 run.

The fabric portion of the structure 10 may be provided with a second plurality of weft strands 66 (see FIG. 6A) which guide the fabric to form a curve as shown in FIG. 5. The second plurality of weft strands 66 may be elastic. As shown in FIGS. 5A and 5B, the second plurality of weft strands 66 may be provided on the inside of the structure 10. FIG. 5A shows a weft strand 50 of the first plurality of weft strands 12 provided with eyelets 54. The eyelets 54 have a second weft strand 52 of the second plurality of weft strands 66 running through. The eyelets 54 therefore guide the second weft strand 52. As shown in FIG. 5B, a weft strand 50 of the first plurality of weft strands 12 may be provided with spacers 56 which has a second weft strand 52 of the second plurality of weft strands 66 going through such that the second weft strand 52 is guided by the spacers 56. The eyelets 54 and/or spacers 56 guide the second plurality of weft strands 66 to create an exact contour of the first plurality of weft strands 12.

Figure 5A:
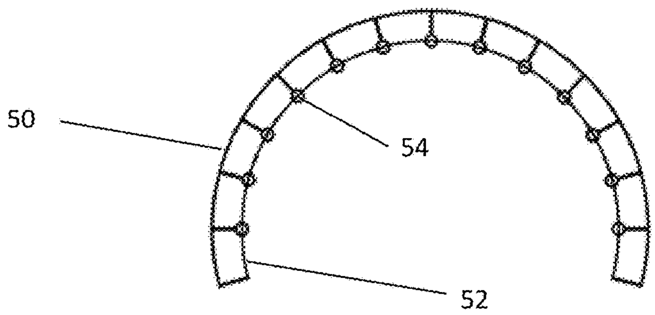
FIGS. 5A to 5F show various weft strand arrangements.
Figure 5B:
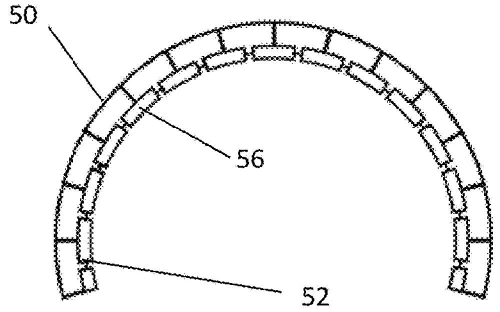
Figure 5C:
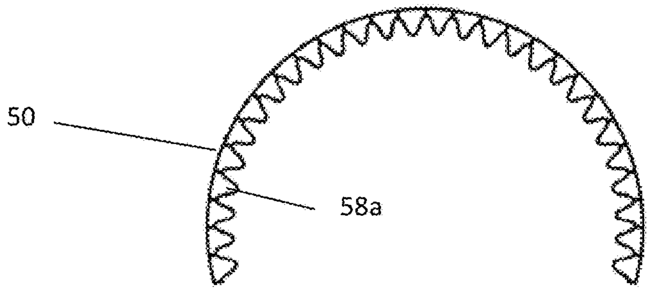
Figure 5D:
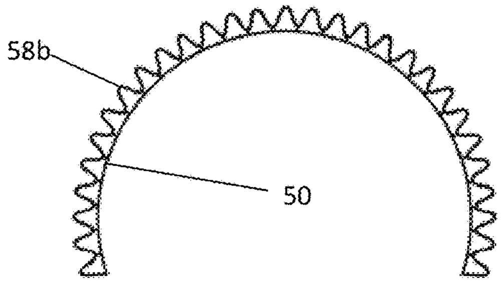
Figure 5E:
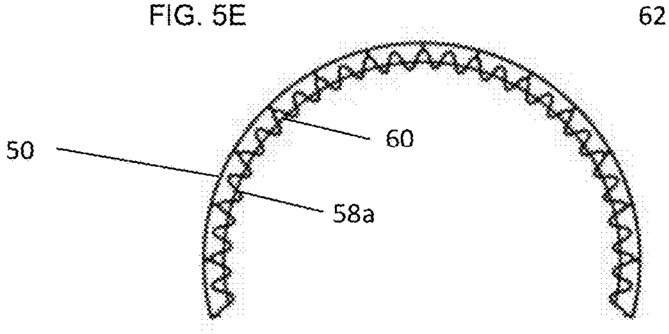

As shown in FIGS. 5C and 5D, the second plurality of weft strands 66 may be springs 58*a* and 58*b*. As shown in FIG. 5C, the spring 58*a* may be provided on the inside of the weft strand 50 of the first plurality of weft strands 12, and may pull the fabric inwards. As shown in FIG. 5D, the spring 58*b* may be provided on the outside of the weft strand 50 of the first plurality of weft strands 12, and may push the fabric outwards. As shown in FIG. 5E, the spring 58*a* may be provided with a cord 60 running through the spring, to prevent the weft strand 50 from flattening out.

Figure 5F:
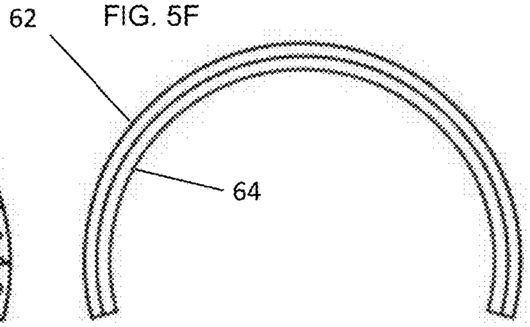

As shown in FIG. 5F, the fabric may comprise a plurality of warp strands 68 which can join a first plurality of weft strands 12 and second plurality of weft strands 66 such that an inner weave 64 and an outer weave 62 are formed. The inner weave 64 pulls the fabric inwards, whilst the outer weave 62 pushes the fabric outwards. The shape and/or movement of the fabric may be controlled by the plurality of weft strands and the at least one warp element alone. Alternatively, the shape and/or movement of the fabric may be enhanced by the provision of one or more cables 18.

Figure 6A:
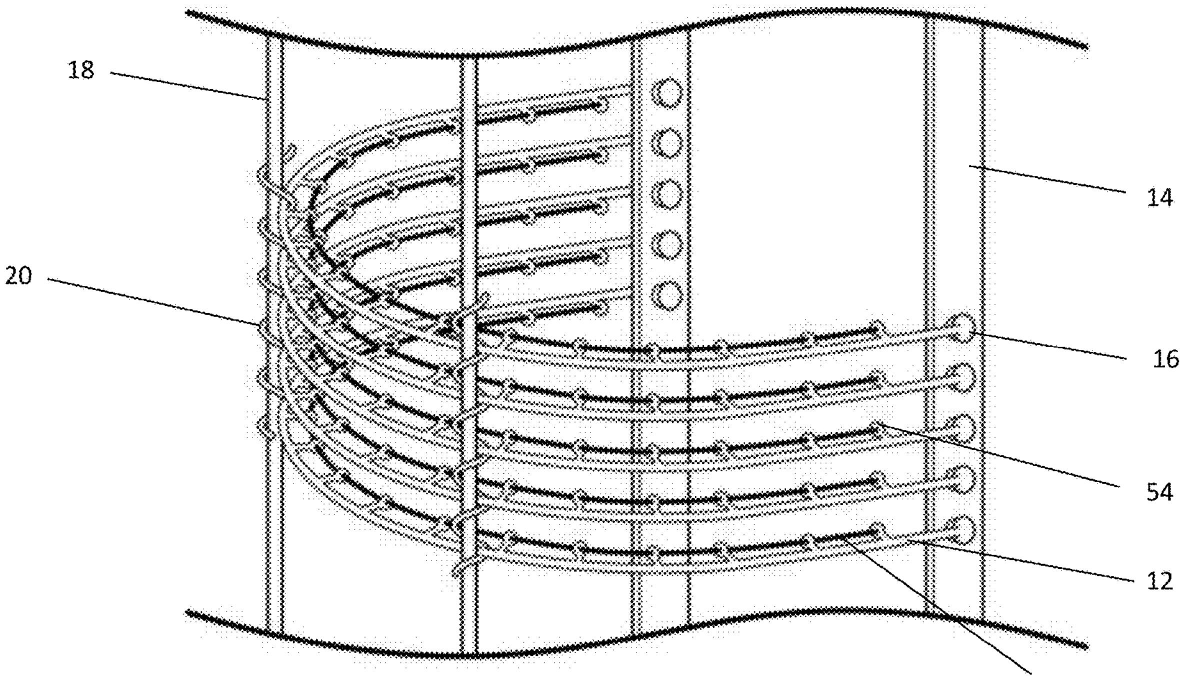
FIG. 6A shows a first and second plurality of weft strands attached to a substantially rigid support.
Figure 6B:
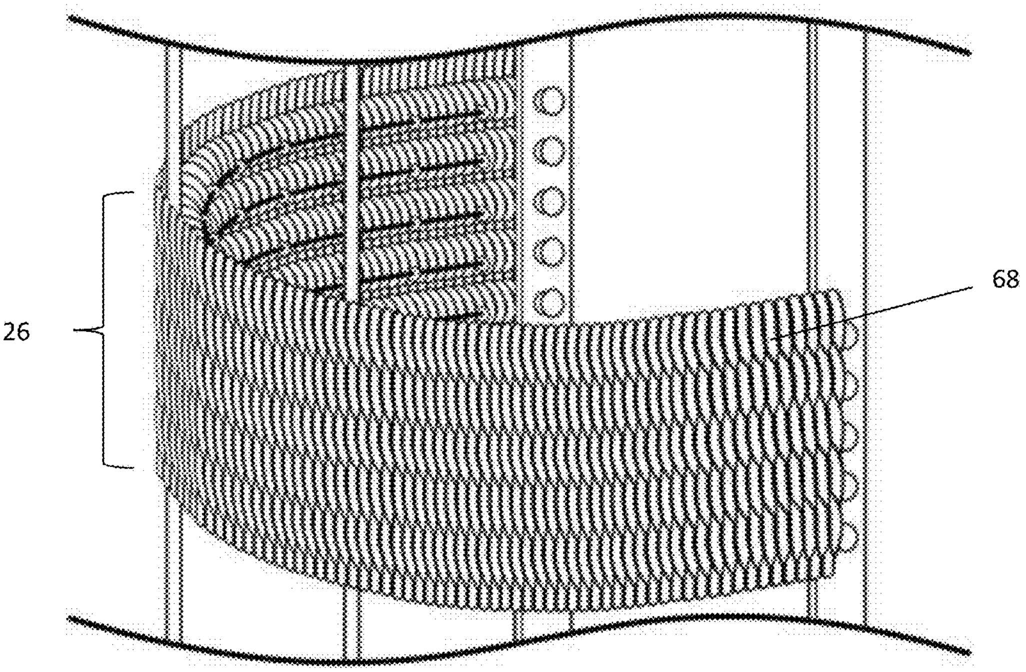
FIG. 6B shows the arrangement of FIG. 6A further comprising a plurality of warp strands.

FIG. 6A shows the arrangement of FIG. 5A with the addition of several cables 18. The cables 18 provide the structure 10 with shape and help to guide the bending of the structure 10 as the prosthetic limb moves. The cables 18 are attached to the first plurality of weft strands 12 such that they are "free-riding" and can slide through the fabric to guide the bending of the structure 10. As shown in FIG. 6A, the cables 18 may be attached to the first plurality of weft strands 12 by spring sheaths 20. Alternatively or additionally, the cables 18 may be attached to the first plurality of weft strands 12 via tube sheaths, eyelets, or may be stitched onto the fabric. Alternatively or additionally, the cables 18 may run through channels 43 in the fabric and/or substantially rigid support 14. FIG. 6B shows the arrangement of FIG. 6A with a plurality of warp strands 68 added such that a woven fabric 26 is formed. The ability of the cables 18 to slide through the fabric with movement of the structure 10 is retained.

Figure 7:
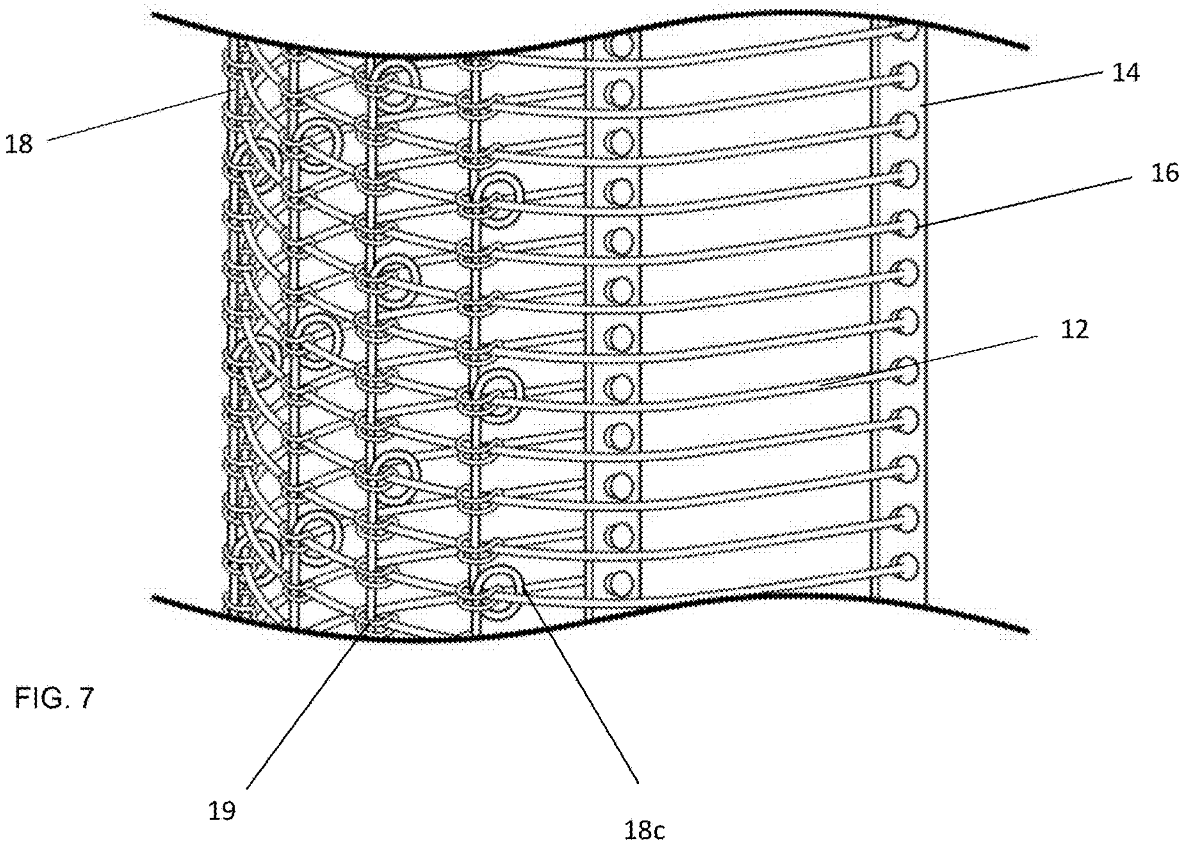
FIG. 7 shows an alternative arrangement for attaching cables to the first plurality of weft strands.

Referring to FIG. 7, an alternative arrangement for attaching the cables 18 to the first plurality of weft strands 12 such that they are "free-riding," is shown. The cables 18 form loops 18*c* intermittently along their path. The cables 18 may form loops 18*c* encompassing one in every three weft strands, in the illustrated example. The loops 18*c* may be offset with the loops 18*c* of the adjacent cables 18. In the arrangement shown in FIG. 7, the cables 18 end at the top and bottom of the structure 10 with loops 18*c*, and therefore there is no need to provide the upper band 30 and/or substantially rigid support 14 with channels to receive the loose ends of the cables 18. The loops 18*c* may be used on their own to attach the cables 18 to the first plurality of weft strands 12. Alternatively, or additionally, the loops 18*c* may be used in combination with stitching 19 to attach the cables 18 to the first plurality of weft strands 12. Alternatively or additionally, the loops 18*c* may be used in combination with eyelets or sheaths to attach the cables 18 to the first plurality of weft strands 12.

As shown in FIG. 8, the plurality of weft and warp strands may have various arrangements. The plurality of weft and warp strands may be made out of silicone. FIGS. 8A and 8B illustrate the first plurality of weft strands 12 and the first plurality of warp strands 68 having an accordion-like arrangement. Each of the first plurality of weft strands 12 is housed in a tube and the tube housings are connected between weft strands 12 such that the tube housing forms the plurality of warp strands 68. As shown in FIGS. 8C and 8D, the first plurality of weft strands 12, the second plurality of weft strands 66 and the first plurality of warp strands 68 may have a zigzag arrangement. As shown in FIGS. 8E and 8F, the plurality of weft strands 12 may be a 3D printed lattice. In the example of 8E and 8F, the plurality of weft strands 12 together form a spring which acts as a contractible/expandable coil in the warp direction. As shown in FIGS. 8G and 8H, the first plurality of weft strands 12, the second plurality of weft strands 66 and the first plurality of warp strands 68 form a double weft weave with looped warp. Cables 18 may be attached to the arrangement shown in FIGS. 8G and 8H by running through the loops created by the warp strands 66 and 68. Alternatively or additionally, cables 18 may be attached by running between two weft strands 12. As shown in FIGS. 81 and 8J, the first plurality of weft strands 12 and the second plurality of weft strands 66, may form a double weft weave with the first plurality of warp strands 68.

Figure 8A:
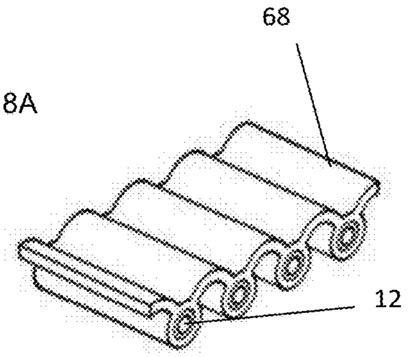
FIGS. 8A to 8J show various arrangements of a plurality of weft and a plurality of warp strands.
Figure 8B:
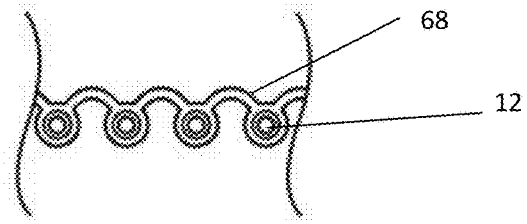
Figure 8C:
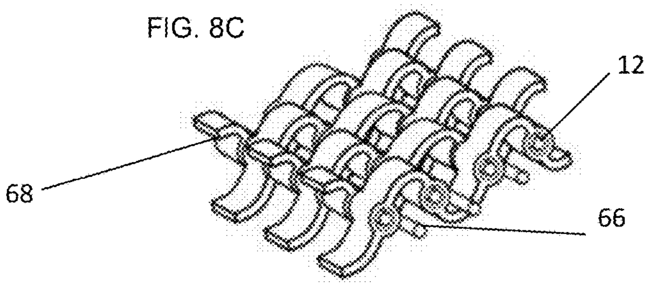
Figure 8D:
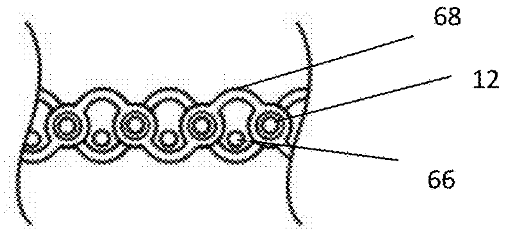
Figure 8E:
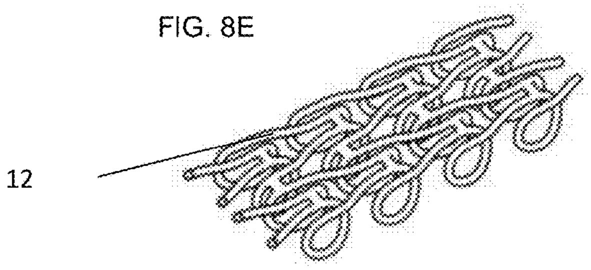
Figure 8F:
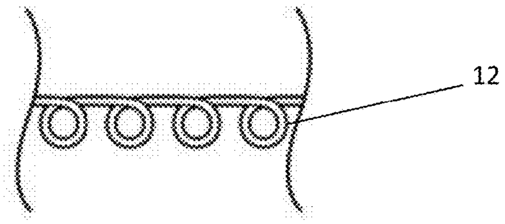
Figure 8G:
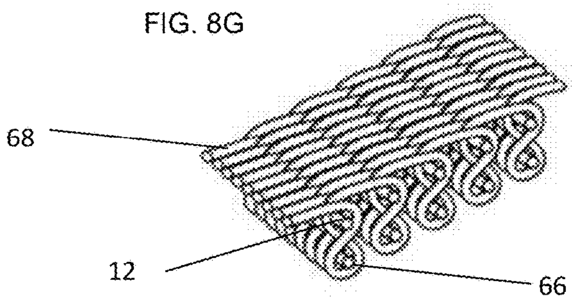
Figure 8H:
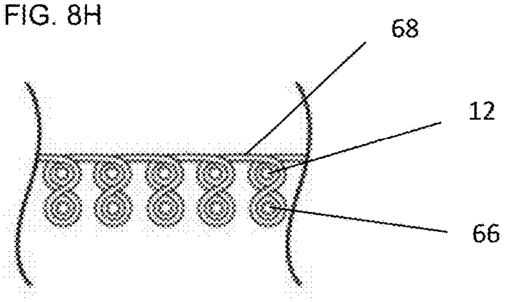
Figure 8I:
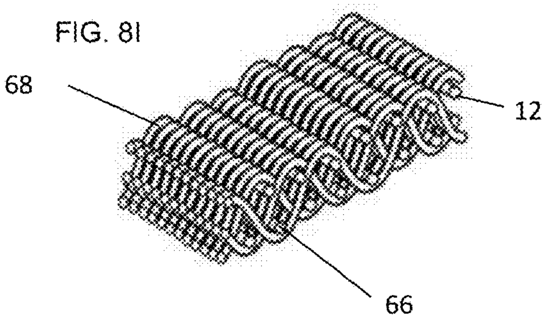
Figure 8J:
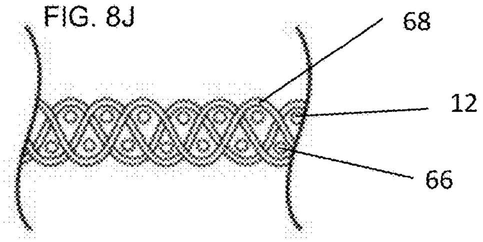
Figure 9:
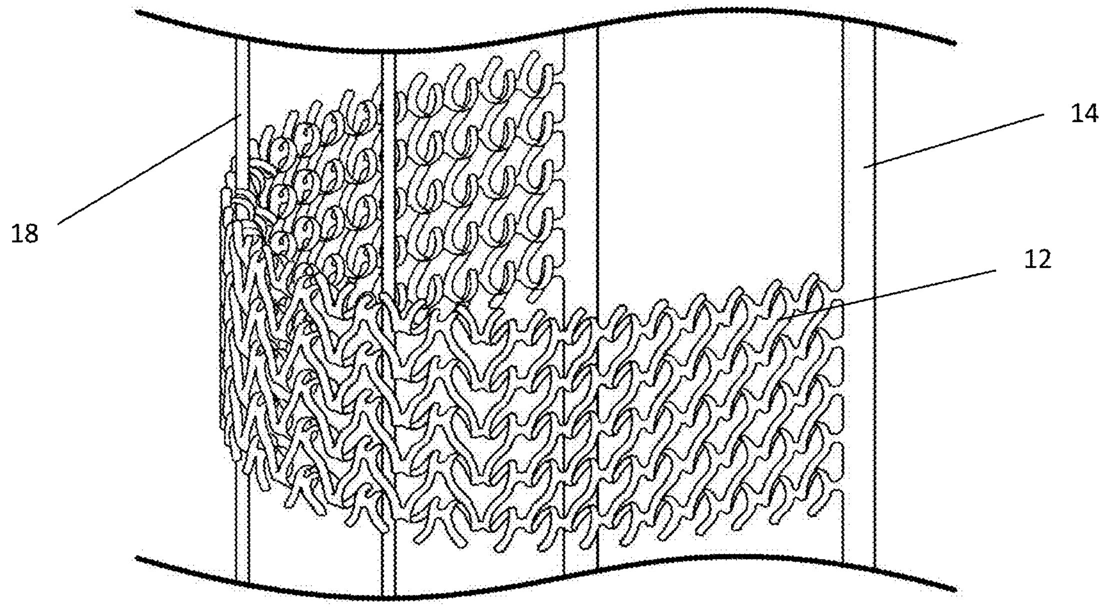
FIG. 9 shows a plurality of weft strands arranged as a 3D lattice.

FIG. 9 shows the arrangement of FIGS. 8E and 8F in which the plurality of weft strands 12 forms a 3D printed lattice structure. As shown in FIG. 9, several cables 18 are attached to the plurality of weft strands 12 of the 3D printed lattice such that they are "free-riding" and can slide through the fabric. The plurality of weft strands 12 of the 3D printed lattice are attached to the substantially rigid support 14 such that the lattice acts as a living hinge. Instead of attaching to the substantially rigid support 14 at a plurality of points 16 such that the individual weft strands pivot/hinge as shown in FIGS. 1 and 6, the 3D printed lattice may be printed as substantially one piece and may attach onto the substantially rigid support 14 via a cooperating means such that it 'snaps' into place. In this arrangement the 3D printed lattice itself provides the fabric with flex as the structure 10 moves and the lattice itself acts as the hinge. The nature of the flex depends on the topology of the lattice. It is possible to achieve a curved bend as desired.

Various further aspects and embodiments of the present invention will be apparent to those skilled in the art in view of the present disclosure.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example with reference to several embodiments. It is not limited to the disclosed embodiments and that alternative embodiments could be constructed without departing from the scope of the invention as defined in the appended claims.

What is claimed is:

1. A structure for covering a prosthetic limb, the structure comprising:

a fabric comprising a plurality of weft strands and at least one warp element;

a substantially rigid support configured to run along the part of the structure which deforms least with movement of the structure; and wherein the plurality of weft strands of the fabric are attached to the substantially rigid support at a plurality of points such that the weft strands pivot independently of the substantially rigid support with movement of the structure.

2. The structure according to claim 1, further comprising one or more cables attached to the plurality of weft strands of the fabric.

3. The structure according to claim 1, wherein the fabric is woven.

4. The structure according to claim 1, wherein the fabric is knitted.

5. The structure according to claim 1, wherein the fabric is 3D printed.

6. The structure according to claim 1, further comprising a second plurality of weft strands.

7. The structure according to claim 1, wherein the structure is substantially hollow.

8. The structure according to claim 1, further comprising an upper band configured for attaching the structure to the prosthetic limb, wherein the upper band is attached to the fabric or to the substantially rigid support of the structure.

9. The structure according to claim 1, wherein the structure further comprises a zip.

10. The structure according to claim 1, wherein the substantially rigid support comprises one or more flexible portions.

11. The structure according to claim 1, further comprising an outer layer.

12. An assembly comprising a prosthetic limb and a structure as claimed in claim 1.

13. The assembly according to claim 12, wherein the prosthetic limb is a prosthetic arm.

14. The assembly according to claim 12, wherein the prosthetic limb is a prosthetic leg comprising one or more of:

an ankle joint;

a knee joint;

a pylon connecting the ankle joint and the knee joint and configured to form a prosthetic shin;

an attachment configured for attaching the prosthetic leg to a residual leg; and a length connecting the knee joint to the attachment for attaching the prosthetic leg to the residual leg, and wherein the length is configured to form a prosthetic thigh.

15. The assembly according to claim 14, wherein the substantially rigid support runs between the ankle joint and the attachment for attaching the prosthetic leg to the residual leg.

16. The assembly according to claim 14, wherein the substantially rigid support runs along the middle of both the inside and outside of the prosthetic thigh, when the prosthetic thigh is viewed from the side.

17. The assembly according to claim 14, wherein the substantially rigid support comprises a flexible portion at the knee joint which curves from the prosthetic thigh to the top of the prosthetic shin.

18. The assembly according to claim 14, wherein the substantially rigid support runs along the prosthetic shin.

19. The assembly according to claim 14, wherein the substantially rigid support runs along the inside and the outside of the prosthetic ankle joint.

20. A structure for covering a prosthetic limb, the structure comprising:

a fabric comprising a plurality of weft strands and at least one warp element;

a substantially rigid support configured to run along a part of the structure which deforms least with movement of the structure;

wherein the substantially rigid support comprises a plurality of apertures substantially evenly spaced along a length of the substantially rigid support;

wherein each aperture of the plurality of apertures receives a portion of a corresponding weft strand of the plurality of weft strands; and wherein the portion of the corresponding weft strand is rotatable within the corresponding aperture to permit planar rotation of the corresponding weft strand relative to the substantially rigid support such that the plurality of weft strands pivot independently of the substantially rigid support with movement of the structure.

* * * * *